United States Patent [19]
Peterson et al.

[11] Patent Number: 5,861,146
[45] Date of Patent: Jan. 19, 1999

[54] METHOD FOR REDUCING BODY ODOR

[75] Inventors: Liezl Gonzales Peterson, Loveland; Toan Trinh, Maineville, both of Ohio

[73] Assignee: The Procter & Gamble Company, Cincinnati, Ohio

[21] Appl. No.: 871,861

[22] Filed: Jun. 9, 1997

[51] Int. Cl.$^6$ .............. A61K 7/32; A61K 33/24; A61K 25/00; A61K 33/10
[52] U.S. Cl. .............. 424/65; 422/5; 422/67; 422/69; 422/76.1; 422/76.2; 422/76.21; 422/76.4; 422/76.8; 422/78.03; 422/405; 422/642; 422/715; 422/717
[58] Field of Search .............. 424/65, 67, 69, 424/76.1, 76.2, 76.21, 76.4, 76.8, 78.03, 405, 642, 715, 717; 422/5

[56] References Cited

U.S. PATENT DOCUMENTS

| | | | |
|---|---|---|---|
| 3,574,821 | 4/1971 | Pfirmann et al. | 424/45 |
| 4,014,995 | 3/1977 | Juliano et al. | 424/168 |
| 4,078,051 | 3/1978 | Pomot et al. | 424/35 |
| 4,278,658 | 7/1981 | Hooper et al. | 424/65 |
| 4,382,079 | 5/1983 | Marschner | 424/65 |
| 4,650,670 | 3/1987 | Callingham et al. | 424/65 |
| 4,659,564 | 4/1987 | Cox et al. | 424/65 |
| 4,659,696 | 4/1987 | Hirai et al. | 514/15 |
| 4,822,602 | 4/1989 | Sabatelli | 424/65 |
| 4,913,896 | 4/1990 | Harvey | 424/69 |
| 5,098,693 | 3/1992 | Faas, Jr. et al. | 424/45 |
| 5,370,875 | 12/1994 | Rogozinski | 424/405 |
| 5,429,628 | 7/1995 | Trinh et al. | 604/359 |
| 5,453,266 | 9/1995 | Malka | 424/65 |
| 5,486,355 | 1/1996 | Berschied, Jr. | 424/65 |
| 5,514,367 | 5/1996 | Lentini et al. | 424/59 |
| 5,518,727 | 5/1996 | Lajoie et al. | 424/400 |
| 5,525,331 | 6/1996 | Betts | 424/65 |
| 5,540,853 | 7/1996 | Trinh et al. | 510/101 |
| 5,552,378 | 9/1996 | Trinh et al. | 512/3 |
| 5,578,563 | 11/1996 | Trinh et al. | 510/513 |
| 5,580,851 | 12/1996 | Trinh et al. | 512/4 |
| 5,593,670 | 1/1997 | Trinh et al. | 424/76.1 |
| 5,635,165 | 6/1997 | Panitch | 424/65 |

FOREIGN PATENT DOCUMENTS

| | | |
|---|---|---|
| 0 701 812 A1 | 3/1996 | European Pat. Off. . |
| 2201880 | 5/1974 | France . |
| 2304156 A | 8/1974 | Germany . |
| 2731520 | 1/1979 | Germany . |
| 229304 A1 | 11/1985 | Germany . |
| HU 208482 B | 8/1992 | Hungary . |
| 53-41440 | 4/1978 | Japan . |
| 58-124452 | 7/1983 | Japan . |
| 61-128973 | 6/1986 | Japan . |
| 63-164953 | 7/1988 | Japan . |
| 3-170415 | 7/1991 | Japan . |
| 3-284616 | 12/1991 | Japan . |
| 5-269185 | 10/1993 | Japan . |
| 7-100644 | 11/1995 | Japan . |
| WO 94/22500 | 10/1994 | WIPO . |
| WO 96/04940 | 2/1996 | WIPO . |

OTHER PUBLICATIONS

H. Matsuda, et al., "Application of 2–Hydroxypropyl–β–Cyclodexytrin to Perfumes and Cosmetics", The 7th International Cyclodextrins Symosium, Tokyo,Japan, Apr. 25–28, 1994, pp. 516–519.

U.S. application No. 08/736,469 Trinh, et al. filed Oct. 24, 1996.
U.S. application No. 08/736,093 Trinh, et al. filed Oct. 24, 1996.
U.S. application No. 08/889,607 Trinh, et al. filed Jul. 8, 1997.
U.S. application No. 08/736,471 Lucas, et al. filed Oct. 24, 1996.
U.S. application No. 08/736,470 Lucas, et al. filed Oct. 24, 1996.
U.S. application No. 08/738,964 Dodd, et al. filed Oct. 24, 1996.
U.S. application No. 08/736,838 Peterson, et al. filed Oct. 28, 1996.
U.S. application No. 08/739,091 Peterson, et al. filed Oct. 28, 1996.
U.S. application No. 08/871,166 Lucas, et al. filed Jun. 9, 1997.
U.S. application No. 08/871,854 Lucas, et al. filed Jun. 9, 1997.
U.S. application No. 08/871, 791 Dodd, et al. filed Jun. 9, 1997.
U.S. application No. 08/871,855 Trinh, et al. filed Jun. 9, 1997.
U.S. application No. 08/871,853 Lucas, et al. filed Jun. 9, 1997.
U.S. application No. 08/871,857 Lucas, et al. filed Jun. 9, 1997.
U.S. application No. 08/871,790 Peterson, et al. Jun. 9, 1997.
U.S. application No. 08/871,856 Peterson, et al. filed Jun. 9, 1997.
U.S. application No. 08/871,858 Lucas, et al. filed Jun. 9, 1997.
U.S. application No. 08/871,577 Lucas, et al. filed Jun. 9, 1997.
U.S. application No. 08/871,860 Lucas, et al. filed Jun. 9, 1997.

(List continued on next page.)

Primary Examiner—Shelley A. Dodson
Attorney, Agent, or Firm—Kirsten K. Stone; Mary Catherine Hentz; Douglas C. Mohl

[57] ABSTRACT

The present invention relates to methods of reducing body and/or vaginal odor comprising the application of a perfumed powder composition comprising from about 0.1% to about 25%, by weight of the composition, of uncomplexed cyclodextrin; a perfume composition selected from the group consisting of from about 0.05% to about 15%, by weight of the odor absorbing composition, of an encapsulated perfume, and from about 0.01% to about 5% by weight of the odor absorbing composition of a free perfume, and mixtures thereof; and a powder carrier.

20 Claims, No Drawings

OTHER PUBLICATIONS

U.S. application No. 08/871,092 Peterson, et al. filed Jun. 9, 1997.
U.S. application No. 08/289,732 Trinh, et al. filed Aug. 12, 1994.
U.S. application No. 08/289,733 Trinh, et al. filed Aug. 12, 1994.
U.S. application No. 08/289,734 Cappel, et al. filed Aug. 12, 1994.
U.S. application No. 08/289,735 Cappel, et al. filed Aug. 12, 1994.
U.S. application No. 08/289,969 Pilosof, et al. filed Aug. 12, 1994.
U.S. application No. 08/871,576 Woo, et al. filed Jun. 9, 1997.
U.S. application No. 08/871,119 Woo, et al. filed Jun. 9, 1997.
U.S. application No. 08/871,042 Woo, et al. filed Jun. 9, 1997.

Hashimoto, H., "Studies on the Industrial Production and Application of Cyclodextrins", Starch Science, vol. 36, No. 1 (1989), pp. 35–42.

Hashimoto, H., "Application of Cyclodextrins to Foods, Toiltries and Other Products in Japan", Ensuiko Sugar Refining Co., Ltd., pp. 13–46.

"Skin Products for Babies", Harry's Cosmeticology, (1982), pp. 112–113, 288–97, 300–04, 757–61, 764–65.

METHOD FOR REDUCING BODY ODOR

BACKGROUND OF THE INVENTION

Body odor is most commonly aused by fatty acids on skin and by malodors from microbial sources. The human skin is naturally populated with numerous micro-organisms which are nourished by various skin secreted substances (eccrine and apocrine sweat, and sebum), skin cell debris, breakdown products of the skin and the organisms themselves. These unpleasant body odors are mainly organic molecules which have different structures and functional groups, such as amines, acids, alcohols, aldehydes, ketones, phenolics, polycyclics, indoles, aromatics, polyaromatics, etc. They can also be made up of sulfur-containing functional groups, such as, thiol, mercaptan, sulfide and/or disulfide groups.

Numerous attempts have been made to control or absorb body odors. Attempts have been made to deprive the microbials responsible for body odor of the moist/humid environment they need to proliferate and grow. Such efforts include the use of powders and/or antiperspirants. Body powders and powder-based compositions of the prior art have limited absorption capabilities. Antiperspirants are not always preferred in a body odor control product since, when used over the entire body, they may interfere with the body's thermal regulatory process by inhibiting perspiration through the action of astringent salts. Additionally, such salts may be irritating to a large number of users, particularly when applying them to sensitive areas such as the pelvic region.

Other deodorant compositions aimed at combating/controlling odor associated with skin secretions, which have been described in the chemical and cosmetic literature, include emulsion sticks or suspensoid sticks, aerosols, roll-ons, pads, pump sprays, and even soap bars. These known deodorants attempt to control odor through a variety of means. For instance, U.S. Pat. No. 5,525,33 1, to Betts, issued Jun. 11, 1996, discloses compositions which inhibit the growth of micro-organisms in the body-secretions. Deodorants may also include antibacterial compounds which help destroy/control the amount of bacteria present on skin, thereby minimizing odor produced via bacterial metabolism of skin secretions.

Zeolites are known odor absorbers. However, these solid odor absorbers, in addition to known activated charcoal odor absorbers, lose functionality when wet. Therefore, when wetted by body fluids or when carried in an aqueous solution, these odor absorbers are not preferred as they lose their desired odor absorbent characteristics. Furthermore, zeolites can cause "harsh" feel if too much is deposited onto the skin.

In addition to the aforementioned attempts at controlling and/or absorbing body odor, numerous attempts have been made to mask body odors with other odors or perfumes. However, perfumes are often inadequate at fully concealing body odors and may be irritating to the user when used alone for odor control.

Thus, there remains a need for an improved method of reducing body and/or vaginal odor using a perfumed odor absorbing composition, which is essentially free of irritating, astringent antiperspirants and which is safe and effective for use on the entire body. More particularly, there is a need for a method of using a composition which is left on the skin to absorb a broad spectrum of body odors that are not fully suppressed by the aforementioned means.

It has been discovered that such enhanced body odor control can be safely provided to the entire body by applying a composition, which is left on the skin, which incorporates odor absorbing, uncomplexed cyclodextrins; perfume composition; and a powder carrier. Surprisingly, it has been discovered that perfume composition may be added without defeating the body odor absorption utility of the uncomplexed cyclodextrins. A particular advantage of the present invention is the ability to provide convenient, non-irritating odor protection when applied to occluded skin areas such as the pelvic region, the external vagina, the panty-area, the bra-line, and skin-folds, which may be very sensitive. Moreover, it has been discovered that the aforementioned benefits may be delivered in a powder carrier which also optionally delivers skin aid benefits to the user such as protection and/or moisturization.

These and other objects of the present invention will become readily apparent from the detailed description which follows. All percentages, ratios, and parts herein, in the Specification, Examples, and Claims are by weight unless otherwise stated. The term "g", as used herein, means gram. The term "ml", as used herein, means milliliter. The term "wt", as used herein, means "weight".

SUMMARY OF THE INVENTION

The present invention relates to methods of reducing body and/or vaginal odor comprising the application of a perfumed powder composition comprising from about 0.1% to about 25%, by weight of the composition, of uncomplexed cyclodextrin; a perfume composition selected from the group consisting of from about 0.05% to about 15%, by weight of the odor absorbing composition, of an encapsulated perfume, and from about 0.01% to about 5% by weight of the odor absorbing composition of a free perfume, and mixtures thereof; and a powder carrier.

DETAILED DESCRIPTION OF THE INVENTION

The present invention relates to methods of reducing body and/or vaginal odor comprising application of an odor-absorbing perfumed powder composition which comprises dry ingredients preferably having particle sizes of from about 1 micron to about 100 microns; more preferred from about 1 micron to about 60 microns; and most preferred from about 1 micron to about 20 microns. As used herein, the particle size refers to the largest dimension of the particle and to the ultimate (or primary) particles. The present invention also relates to methods of use of an article of manufacture comprising the compositions herein deposited on a flexible dispensing means.

The term "occluded skin", as used herein, refers to regions of a human or mammalian body covered by undergarments, such as the pelvic area, panty-area, and bra-line; and skin-folds or intertriginous regions, where there is continuing skin to skin contact. The term "excess moisture", as used herein, means an undesirable and/or unhealthy level of body fluids deposited on the skin. The term "body fluids", as used herein, includes eccrine sweat, apocrine sweat, sebum, build up of sensible moisture from transepidermal water loss, vaginal discharge, urine, and mixtures thereof. The term "body odor" as used herein means odors which are generated as a result of the natural functioning of a human or mammalian body. Such odors include, but are not limited to odors produced by microorganisms of the skin (i.e. bacterial decomposition of skin secretions), urine, or vaginal discharge, and mixtures thereof. The term "skin" means human or mammalian skin. The term "entire body" means the entire external surface of human or mammalian skin. The term "vaginal odor" relates specifically to those body odors which emanate from the pelvic region of a woman, particularly the vagina and the panty line.

A detailed description of essential and optional components of the present invention is given below.

CYCLODEXTRIN: As used herein, the term "cyclodextrin" includes any of the known cyclodextrins such as unsubstituted cyclodextrins containing from six to twelve glucose units, especially alpha-cyclodextrin, beta-cyclodextrin, gamma-cyclodextrin and/or their derivatives and/or mixtures thereof. The term "uncomplexed cyclodextrin" as used herein means that the cavities within the cyclodextrin in the composition of the present invention should remain essentially unfilled prior to application to skin in order to allow the cyclodextrin to absorb various odor molecules when the composition is applied to the skin.

Preferred cyclodextrins for use in the present invention are alpha-cyclodextrin, beta-cyclodextrin, gamma-cyclodextrin and/or their derivatives. More preferred are beta cyclodextrin, hydroxypropyl alpha-cyclodextrin, hydroxypropyl beta-cyclodextrin, methylated-alpha-cyclodextrin or methylated-beta-cyclodextrin. Most preferred is beta-cyclodextrin.

It is also preferable to use a mixture of cyclodextrins. Such mixtures absorb body odors more broadly by complexing with a wider range of odoriferous molecules having a wider range of molecular sizes. The levels of cyclodextrin are from about 0.1% to about 25%, preferably from about 1% to about 20%, more preferably from about 2% to about 15%, most preferably from about 3% to about 10%, by weight of the composition.

The complexation between cyclodextrin and odorous molecules occurs rapidly when wetted with body fluids. This is convenient for the user because the cyclodextrins, while on dry skin, will not fill their cavities with other environmental odors which would otherwise render them less efficient for absorbing body odors. More particularly, upon solubilization of the cyclodextrins by the body fluids, the isolated cavities become available to form inclusion complexes with the body odor molecules. Thus, ultimately, the availability of solubilized uncomplexed cyclodextrin is essential for an effective and efficient odor control performance.

Cyclodextrins having small particle sizes aid in providing higher cyclodextrin surface availability for odor absorption and therefore are preferred. As used herein, the particle size refers to the largest dimension of the particle and to the ultimate (or primary) particles. Small particle cyclodextrins of this invention are those having a particle size of less than about 12 microns, preferably less than about 10 microns, and more preferably less than about 5 microns. A more complete description of the cyclodextrins, cyclodextrin derivatives, and cyclodextrin particle sizes useful in the present invention can be found in U.S. Pat. No. 5,429,628, Trinh et al., issued Jul. 4, 1995, which is incorporated herein by reference in its entirety.

PERFUME COMPOSITION: Perfume is an essential component of the present invention and is included at a level which is non-irritating to the ordinary user's skin and/or respiratory tract, yet is discernible by the human sense of smell either before and/or after application to the skin. The perfume compositions should be safe for use on skin. The perfume compositions useful herein are comprised of perfume ingredients. The perfume compositions can be either in the form of free perfume, in the form of encapsulated perfume, or mixtures thereof. The perfume composition is typically present at a level of from about 0.01% to about 20% by weight of the odor absorbing composition.

Encapsulated Perfume: It is preferred that an effective amount, typically from about 0.05% to about 15%, preferably from about 0.1% to about 10%, more preferably from about 0.2% to about 8%, and even more preferably from about 0.5% to about 5%, by weight of the odor absorbing composition, be in the form of encapsulated perfume. Encapsulating perfume helps prevent premature loss of the perfume composition to the atmosphere as well as helping avoid strong odor which can be uncomfortable to the user. As used herein, the phrase "encapsulated perfume" refers to perfume compositions which are contained in or, preferably, encapsulated in a carrier. Examples of encapsulation means suitable for forming the encapsulated perfume herein include formation of cyclodextrin/perfume ingredient inclusion complexes, coacervate encapsulation, cellular matrix encapsulation, crude formation of perfume-filled porous particles, and mixtures thereof. The encapsulated perfumes are preferably those which are released by a moisture activation mechanism whereby upon being wetted, e.g., by perspiration or other body fluids, the encapsulated perfume releases the perfume composition. Thus, skin irritation caused by perfume is minimized as encapsulated perfume is released only when wetted.

Cyclodextrin/perfume ingredient inclusion complexes are preferred not only because they display the preferred moisture activation release, but also for their effectiveness and ease of processing. Perfume loading in the cyclodextrin complex is fairly low, e.g., from about 10% to about 18% in beta-cyclodextrin/perfume complex. The cyclodextrin/perfume ingredient inclusion complexes, particle sizes, and methods of formation useful herein, are disclosed in detail in U.S. Pat. No. 5,429,628, Trinh et al., issued Jul. 4, 1995, which is incorporated herein by reference in its entirety. At least an effective amount of the cyclodextrin/perfume ingredient inclusion complex is to be applied to the odor absorbing compositions herein in order to deliver the desired levels of perfume composition. Effective amounts are typically in the range of from about 0.01% to about 10%, preferably from about 0.1% to about 3%, more preferably from about 0.2% to about 2%, by weight of the odor absorbing composition.

Coacervate perfume encapsulation is a commonly known encapsulation method wherein a droplet of one or more perfume ingredients is enclosed in a solid wall material. In cellular matrix perfume encapsulation, a solid particle contains many small droplets of one or more perfume ingredients stably held in the cells. Water-soluble (moisture-activated) cellular matrix perfume microcapsules which are preferred for use herein, and preparation thereof, are described in detail in U.S. Pat. No. 5,429,628, Trinh et al., issued Jul. 4, 1995, which is incorporated herein by reference in its entirety. Water-soluble cellular matrix perfume microcapsules useful in the present invention preferably have size of from about 0.5 micron to about 60 microns, more preferably from about 1 micron to about 50 microns, most preferably from about 2 microns to about 40 microns.

Coacervate perfume encapsulation and cellular matrix perfume encapsulation are preferred for their perfume loading which can be as high as 60%–80%. Effective amounts of coacervate and/or cellular matrix perfume microcapsules are typically in the range of from about 0.002% to about 6%, preferably from about 0.007% to about 1%, more preferably from about 0.01% to about 0.5%, by weight of the odor absorbing composition.

The crudely formed perfume-filled porous particles are used when a slow, continuous perfume composition release is desired. The perfume-filled porous particles are perfume ingredients/compositions which are more crudely embedded in a matrix and which release via diffusion. Starch matrix perfume-filled porous particles can be prepared according to the disclosure in U.S. Pat. No. 5,267,531, Appel et al., issued Dec. 7, 1993, which is incorporated herein by reference in its entirety. A nonlimiting example of useful porous particles, starch granules, are disclosed by Whistler et al., *Food Technology*, July 1994, pp. 104–105, incorporated herein by reference. The perfume-filled porous particles can be coated with suitable materials to improve perfume ingredient retention. The preferred particle size for the porous particle is from about 10 microns to about 60 microns, more preferably from about 15 microns to about 40 microns.

Preferably, the encapsulated perfume, whatever form it takes, is composed of perfume ingredients selected predominantly from two groups of ingredients, namely, (a) volatile perfume ingredients having a boiling point at normal pressure of less than about 260° C., more preferably less than about 250° C., and (b) ingredients having significant low odor detection threshold, and mixtures thereof. The boiling points of many perfume ingredients are given in, e.g., "Perfume and Flavor Chemicals (Aroma Chemicals)," Steffen Arctander, published by the author, 1969, incorporated herein by reference in its entirety. Typically, at least about 50%, preferably at least about 60%, more preferably at least about 70%, and most preferably at least about 80% by weight of the encapsulated perfume is composed of perfume ingredients of the above groups (a) and (b).

Nonlimiting examples of the more preferred volatile perfume ingredients are allo-ocimene, allyl caproate, allyl cyclohexaneacetate, allyl cyclohexanepropionate, allyl heptanoate, amyl acetate, amyl propionate, anethol, anisic aldehyde, anisole, benzaldehyde, benzyl acetate, benzyl acetone, benzyl alcohol, benzyl butyrate, benzyl formate, benzyl iso valerate, benzyl propionate, beta gamma hexenol, butyl benzoate, butyl caproate, 4-tert-butylcyclohexyl formate, camphene, camphor gum, carvacrol, laevo-carveol, d-carvone, laevo-carvone, cinnamyl formate, cis-jasmone, cis-3-hexenyl acetate, cis-3-hexenyl butyrate, cis-3-hexenyl caproate, cis-3-hexenyl tiglate, cis-3-hexenyl valerate, citral (neral), citronellol, citronellyl acetate, citronellyl formate, citronellyl isobutyrate, citronellyl nitrile, citronellyl oxyacetaldehyde, citronellyl propionate, cuminic alcohol, cuminic aldehyde, Cyclal C, cyclohexyl ethyl acetate, beta-damascone, 2-decenal, decyl aldehyde, dihydro myrcenol, dihydromyrcenyl acetate, dimethyl benzyl carbinol, dimethyl benzyl carbinyl acetate, dimethyl benzyl carbinyl propionate, dimethyl phenylethyl carbinyl acetate, 3,7-dimethyloctanal, dimethyl octanol, diphenyl oxide, ethyl acetate, ethyl aceto acetate, ethyl amyl ketone, ethyl benzoate, ethyl butyrate, ethyl hexyl ketone, ethyl phenyl acetate, eucalyptol, fenchyl acetate, fenchyl alcohol, flor acetate (tricyclo decenyl acetate), frutene (tricyclo decenyl propionate), gamma methyl ionone, gamma-nonalactone, geraniol, geranyl acetate, geranyl acetoacetate, geranyl butyrate, geranyl formate, geranyl isobutyrate, geranyl nitrile, geranyl propionate, heptyl acetate, heptyl isobutyrate, heptyl propionate, hexenol, hexenyl acetate, hexenyl isobutyrate, hexyl acetate, hexyl formate, hexyl isobutyrate, hexyl isovalerate, hexyl neopentanoate, hexyl tiglate, hydratropic alcohol, hydroxycitronellal, alpha-ionone, beta-ionone, gamma-ionone, alpha-irone, isoamyl alcohol, isobomyl acetate, isobornyl propionate, isobutyl benzoate, isobutyl caproate, isononyl acetate, isononyl alcohol, isomenthol, isomenthone, isononyl acetate, isopulegol, isopulegyl acetate, isoquinoline, lauric aldehyde (dodecanal), lavandulyl acetate, ligustral, d-limonene, linalool, linalool oxide, linalyl acetate, linalyl butyrate, linalyl isobutyrate, linalyl formate, linalyl propionate, menthone, menthyl acetate, methyl acetophenone, methyl amyl ketone, methyl anthranilate, methyl benzoate, methyl benzyl acetate, methyl chavicol, methyl eugenol, methyl heptenone, methyl heptine carbonate, methyl heptyl ketone, methyl hexyl ketone, alpha-iso "gamma" methyl ionone, methyl nonyl acetaldehyde, methyl octyl acetaldehyde, methyl octyl ketone, methyl phenyl carbinyl acetate, methyl salicylate, myrcene, myrcenyl acetate, neral, nerol, neryl acetate, nonalactone, nonyl butyrate, nonyl alcohol, nonyl acetate, nonyl aldehyde, octalactone, octyl acetate, octyl alcohol (octanol-2), octyl aldehyde, orange terpenes (d-limonene), para-cresol, para-cresyl methyl ether, para-cymene, para-isopropyl para-methyl acetophenone, phenethyl anthranilate, phenoxy ethanol, phenyl acetaldehyde, phenyl ethyl acetate, phenyl ethyl alcohol, phenyl ethyl dimethyl carbinol, alpha-pinene, beta-pinene, alpha-terpinene, prenyl acetate, propyl butyrate, pulegone, rose oxide, safrole, alpha-terpinene, gamma-terpinene, 4-terpinenol, terpineol, terpinolene, terpinyl acetate, terpinyl propionate, tetrahydro linalool, tetrahydro myrcenol, thymol, delta-undecalactone, gamma-undecalactone, undecanal, undecenal, undecyl alcohol, Veratrol, Verdox, Vertenex, and viridine.

Nonlimiting examples of other preferred volatile perfume ingredients which can be used in perfume compositions of this invention are amyl benzoate, beta-caryophyllene, cinnamic alcohol, diphenyl methane, dodecalactone, ethyl methyl phenyl glycidate, eugenol, fenchyl acetate, gamma-n-methyl ionone, heliotropine, indole, isobutyl quinoline, Lilial (p-t-Bucinal), methyl-N-methyl anthranilate, para-methoxy acetophenone, phenethyl butyrate, phenyl heptanol, phenyl hexanol, and phenoxy ethyl proprionate.

Preferred encapsulated perfume composition contain at least 5, preferably at least 6, more preferably at least 7, and even more preferably at least 8 different volatile perfume ingredients. Most common perfume ingredients which are derived from natural sources are composed of a multitude of components. When each such material is used in the formulation of encapsulated perfume compositions of the present invention, it is counted as one single ingredient, for the purpose of defining the invention.

The use of small amounts of perfume ingredients that have low odor detection threshold values can improve perfume odor character, even though they are not as volatile as perfume ingredients of group (a) which are given hereinabove. The phrase "odor detection threshold" of an odorous material means the lowest vapor concentration of that material which can be olfactorily detected. The odor detection threshold and some odor detection threshold values are discussed in, e.g., "Standardized Human Olfactory Thresholds", M. Devos et al, IRL Press at Oxford University Press, 1990; and "Compilation of Odor and Taste Threshold Values Data", F. A. Fazzalari, editor, ASTM Data Series DS 48A, American Society for Testing and Materials, 1978, both of said publications being incorporated by reference. Perfume ingredients that do not belong to group (a) above, but have a significantly low odor detection threshold useful herein, are selected from the group consisting of ambrox dl, bacdanol, benzyl salicylate, calone, cetalox, cis-3-hexenyl salicylate, cymal, ebanol, ethyl anthranilate, ethyl methyl phenyl glycidate, ethyl vanillin, dihydro iso jasmonate, gamma dodecalactone, flor acetate, florhydral, frutene, heliotropine, alpha ionone, beta ionone, iso eugenol, alpha isomethylionone, lilial, lyral, methyl dihydrojasmonate, methyl beta naphthyl ketone, beta naphthol methyl ether, para hydroxy phenyl butanone, undecalactone gamma, vanillin., and mixtures thereof. These materials are preferably present at low levels in addition to the volatile ingredients of group (a), typically less than about 20%, preferably less than about 15%, more preferably less than about 10%, by weight of the perfume composition.

There are also volatile ingredients of group (a) that have a significantly low odor detection thresholds which are useful herein. Examples of these ingredients are allyl amyl glycolate, anethol, benzyl acetone, butyl anthranilate, cinnamic alcohol, cyclal C, cyclogalbanate, 4-decenal, ethyl-2-methyl butyrate, eugenol, damascenone, alpha damascone, fructone, herbavert, indole, iso cyclo citral, keone, linalool, methyl anthranilate, methyl heptine carbonate, methyl isobutenyl tetrahydropyran, methyl nonyl ketone, nerol, para anisic aldehyde, phenyl acetaldehyde, and undecylenic aldehyde.

Free Perfume: The perfume composition may also be in the form of a free perfume. The term "free perfume", as used herein, means a perfume composition which is not encapsulated. Where desired, the free perfume may be diluted in a solvent to aid in incorporation into the compositions herein. Suitable solvents include the skin aids disclosed herein and solvents found in the *Cosmetic Bench Reference,* 1994 Edition, page 54, which is incorporated herein by reference. Free perfume may be composed of conventional perfume ingredients at a level of from about 0.01% to about 5%, preferably from about 0.05% to about 3%, more preferably from about 0.05% to about 2%, and most preferably from about 0.1% to about 1%, by weight of the odor absorbing composition.

POWDER CARRIER: The cyclodextrins useful in the present invention should be dispersed in a pharmaceutically-acceptable powder carrier for convenient, uniform application and disbursement onto the skin. The term "pharmaceutically-acceptable", as used herein, means a powder suitable for topical use on the skin without undue toxicity, irritation, allergic response, and the like. The powder carrier also helps prevent any solubilized cyclodextrin from washing away from the desired skin contact. Powder carriers useful in the present invention include powders known in the art to be safe for human skin. Such powders include but are not limited to cornstarch (topical starch), talc, rice starch, oat starch, tapioca starch, microcrystalline cellulose (for example Avicel®), aluminum starch octenyl succinate (sold by National Starch & Chemical Co. as Dry Flo® Pure, Dry Flo® XT, and/or Dry Flo® PC), kaolin, and mixtures thereof. Preferred is cornstarch. The powder carrier of the present invention will comprise from about 10% to about 99%, preferably from about 15% to about 80%, more preferably from about 25% to about 50%, by weight of the composition.

ADJUNCT ODOR CONTROLLING AGENTS: Optionally, the compositions of the present invention may comprise zeolites, carbon odor-controlling agents, sodium bicarbonates, antimicrobial agents and/or antiperspirant ingredients for added body odor control.

The term "zeolite", as used herein, refers to non-fibrous zeolites. When included in the present invention, zeolites may be present from about 0.1% to about 25%, preferably from about 1% to about 15%, by weight of the composition. A detailed description of zeolites useful in the present invention is found in U.S. Pat. No. 5,429,628, Trinh et al., issued Jul. 4, 1995, incorporated herein by reference in its entirety.

Carbon odor-controlling agents described in U.S. Pat. No. 5,429,628 may be used in the present invention at a level of from about 0.1% to about 25%, by weight of the composition.

Alkali metal carbonate and/or bicarbonate salts, such as sodium bicarbonate, potassium bicarbonate, potassium carbonate, cesium carbonate, sodium carbonate, and mixtures thereof, may be added to the powder composition of the present invention in order to help to control acid-type odors. An example of sodium bicarbonate and its use as an underarm deodorant is found in U.S. Pat. No. 4,382,079, to Marschner, issued May 3, 1983, which is incorporated herein in its entirety by reference. Preferred salts are sodium carbonate monohydrate, potassium carbonate, sodium bicarbonate, potassium bicarbonate, and mixtures thereof. Alkali metal carbonate and bicarbonate salts are typically present at a level of from about 0.1% to about 30%, preferably from about 0.2% to about 20%, more preferably from about 0.3% to about 10%, by weight of the powder composition.

The antimicrobial agents of the present invention are selected from a group consisting of antibacterial agents, antifungal agents, and mixtures thereof. Antimicrobial agents help destroy and/or control the amount of bacteria and/or fungi present on the skin. Preferred antimicrobial agents are zinc phenolsulfonate, zinc oxide, triclosan, Zelec® AM by DuPont, zinc ricinoleate, zinc undecylenate, and mixtures thereof. More preferred are zinc phenolsulfonate, zinc oxide, and triclosan. Triclosan is available from Ciba-Geigy as Irgasan DP-300. Examples of antimicrobial agents useful in the present invention are found in the *Cosmetic Bench Reference,* 1994 Edition, page 10, which is incorporated herein by reference. When included in the present invention, the antimicrobials are at a level of from about 0.01% to about 25%. Preferably from about 0.1% to about 10%, by weight of the present composition.

When used on the underarms, antiperspirant ingredients may be included in the present invention. Examples of antiperspirants known in the art are found in the *Cosmetic Bench Reference,* 1994 Edition, page 13, which is incorporated herein by reference. When included in the present invention, antiperspirants may be present from about 0.1% to about 25%, by weight of the composition.

SKIN AIDS: The compositions of the present invention also optionally include skin aids. The term "skin aids", as used herein, refers to skin protectants, emollients, and moisturizers.

Skin protectants useful in the present invention are found in the *Cosmetic Bench Reference,* 1994 Edition, page 53; and the Monograph on Skin Protectant Drug Products for Over-the-Counter Human Use, 21 CFR 347. Preferred skin protectants are corn starch, kaolin, mineral oil, sodium bicarbonate, dimethicone, zinc oxide, colloidal oatmeal, and mixtures thereof. When present, the skin protectants comprise from about 0.1% to about 80%, preferably from about 0.1% to about 30%, most preferably from about 0.1% to about 10%, by weight of the composition.

Emollients and moisturizers useful in the present invention can be found in the *Cosmetic Bench Reference,* 1994 Edition, pages 27–32 and 46–48, incorporated herein by reference. Preferred emollients and moisturizers are tocopherol, tocopheryl acetate, aloe, vegetable oils, mineral oil, petrolatum, jojoba oil, and mixtures thereof. More preferred are encapsulated or spray/freeze dried emollients. The use of spray/freeze dried or encapsulated emollients keeps the emollients protected in the powder carrier until they are released through shearing (such as rubbing against undergarments or clothes) or through contact with skin moisture. Examples of preferred commercial spray/freeze dried aloe useful in the present invention are Terra-Dry™

Freeze Dried Aloe, Terra-Pure™ Freeze or Spray Dried Aloe, and Terra-Spray™ Spray Dried Aloe, all from Terry Laboratories. When present, the skin aids comprise from about 0.1% to about 50%, preferably from about 0.1% to about 25%, most preferably from about 0.1% to about 10%, by weight of the composition.

SLIP COMPOUNDS: The present compositions may optionally comprise slip compounds. The term "slip compounds", as used herein, refers to compounds which have unique structures which provide enhanced slip/lubrication characteristics of powders and/or reduced skin to skin friction between intertriginous skin sites.

Slip compounds of the present invention include polyethylene; nylon; polytetrafluoroethylene; silica which is in the form of microspheres, ellipsoids, barrel-shapes, and the like; mica, silicone (e.g. dimethicone) and metallic stearates (e.g. zinc stearate); and mixtures thereof. Preferred slip compounds are silicas which are in the form of microspheres, ellipsoids, barrel-shapes, and the like. Silica ellipsoids useful in the present invention are available from DuPont as ZELEC® Sil. Silica microspheres are available from KOBO as MSS-500, MSS 500/3, MSS-500/H, MSS-500/3H, MSS-500/N, and MSS-500/3N. Additionally, it is preferred that some of the silica of the present invention be fumed silica for increased flowability of the powder in addition to enhancing the slip characteristics. Fumed silica is available from Cabot Corporation (Cab-O-Sil®) and from Degussa (Aerosil®). When present in the compositions of the invention, the slip compounds comprise from about 0.1% to about 35%, preferably from about 1% to about 10%, by weight of the composition.

BINDERS: The present invention may optionally also include dry or wet binders to help promote adhesion of the powder and active ingredients to the skin. Binders useful in the present invention are found in the *Cosmetic Bench Reference,* 1994 Edition, pages 13–14, which is incorporated herein by reference. Preferred binders calcium stearate, zinc stearate, isopropyl myristate, magnesium myristate, silicone, and mixtures thereof. More preferred are zinc stearate, dimethicone, and mixtures thereof. When included in the composition, the binders are at a level of from about 0.1% to about 25%, preferably from about 1% to about 15%, by weight of the composition.

ANTI-PRURITIC AGENTS: Anti-pruritic agents such as those known in the art may be included in the compositions of the present invention. Examples of anti-pruritic agents useful in the present invention are Magnesium-L-Lactate, hydrocortisone, hydrocortisone acetate, and colloidal oatmeal. A description of anti-pruritic agents are found in the *Handbook of Non Prescription Drugs,* 10th Edition, p. 529, 1993; which is incorporated herein by reference. When included in the composition, anti-pruritic agents may be present from about 0.1% to about 40%, by weight of the composition.

COLORANTS: Colorants and dyes can be optionally added to the odor absorbing compositions for visual appeal and performance impression. Colorants suitable for use in the present invention are found in the *Cosmetic Bench Reference,* 1994 Edition, pages 21–22, which is incorporated herein by reference.

PROCESS OF MAKING COMPOSITIONS

The compositions of the present invention are prepared by the following steps: creating a mixture by mixing cyclodextrin and optional ingredients in a powder carrier via a commercially available mixer such as a vee-blender, double cone blender, or ribbon blender until the mixture is uniform; and creating a reduced size mixture using a commercially available size reduction technique such as hammer milling, impact milling, ball milling, or fluid energy milling until the desired particle size distribution is achieved.

Perfume composition, whether encapsulated or free, may be added to the present compositions in many different ways. One suitable method of including encapsulated perfume involves forming cyclodextrin complexes in the manner described in U.S. Pat. No. 5,429,628, to Trinh et al., issued Jul. 4, 1995, which is incorporated herein by reference, and blending the perfume/cylcodextrin complexes with the composition above in a final or in an intermediate step. Where desired, free perfume may be incorporated by spraying the cyclodextrin, carrier, or any of the powder ingredients with the free perfume. Preferably, the free perfume is blended with one or more of the liquid ingredients herein, such as the skin aids, prior to the spraying.

Since the compositions of the present invention are to be applied directly to the skin or hair, various applicators are useful for delivering the compositions to the entire body for maximum odor control. For example, the compositions are preferably deposited in a bottle, a canister, a spray dispenser, a manually activated spray dispenser, or on a wipe structure which later is contacted with the skin to transfer the composition to the skin. Bottles and canisters known in the art are suitable for use in delivering the compositions of the present invention. Bottles and canisters preferably comprise lids with small apertures for convenient dispensing of the composition.

The composition of the present invention can also be delivered as a suspended solution via a spray dispenser or a bottle, such that when applied or sprayed onto the skin, the solvent would immediately dry/volatilize off to leave a powder film. Examples of such suspension forms are aerosols, liquid powder suspensions, or silicone suspensions. When present in an aerosol composition, the powders of the present invention will usually be present in the range of from about 0.1% to about 15%, by weight of the composition. The incorporation of a powder into an aerosol is more fully explained in U.S. Pat. No. 4,078,051, to Pomot et al., issued Mar. 7, 1978; which is incorporated herein by reference in its entirety. This method is not preferred however for use on sensitive areas of the body such as the panty-area or other occluded skin areas since skin irritations may result from propellants commonly used in aerosol containers.

Preferred is a manually activated spray dispenser which delivers the composition as a powder without the use of propellants, and without the composition being in a solution form. Spray dispensers useful herein are described more fully in U.S. Pat. No. 2,450,205, to Rose, issued Sep. 28, 1948; and U.S. Pat. No. 2,840,277, to Bach, issued Jun. 24, 1958, both of which are incorporated herein by reference in their entireties.

Any wipe structures and/or methods of making the wipe structures commonly known in the art may be used. The wipe comprises a flexible dispensing means. The term "flexible dispensing means", as used herein, includes papers, cloths, non-wovens, films, foams, sponges, rollers, pads, tissues, cotton balls, and the like. Preferred wipe substrates comprise a porous material, such as the non-woven substrates, foams, or sponges, which are capable of holding the composition within the pores of the substrates. Examples of cellulosic non-wovens are described in U.S. Pat. No. 4,191,609, Trokhan, issued Mar. 4, 1980, which is incorporated herein by reference in its entirety.

Packages suitable for use herein are any commonly known in the art and include resealable packages and those suitable for one time use.

Techniques for combining the wipe substrates with the composition of the present invention are well known in the art. Examples of common techniques include coating, immersing, dipping, sprinkling, or spraying, the wipe substrate with the compositions herein. The composition of the present invention is added to the wipe substrate at a level sufficient to provide the desired odor control and/or other desired skin benefits.

METHODS OF USE

The present invention also encompasses a method of reducing body odor comprising the application of an effective amount of the compositions described herein to skin. The present invention also encompasses a method of reducing vaginal odor comprising applying an effective amount of the compositions described herein onto a pelvic region, external vagina, and/or panty-area. However, the compositions of the present invention should not be inserted into the vagina, nor applied onto the vulva. An "effective amount" of the compositions of the present invention, as used herein, means an amount sufficient to absorb body odor so that it is less noticeable by the human sense of smell. While the determination of an effective amount used and the number of uses per day is ultimately left to the discretion of the user, typically an effective amount will be from about 1 cc (cubic centimeter) to about 3 cc of odor absorbing composition per use, applied about 1 to about 3 times daily, for as many days as desired by user.

The compositions herein are topically applied directly to the skin or hair. The compositions can be delivered by placing the composition into a dispensing means and applying an effective amount via spraying, sprinkling, shaking, or rubbing the composition onto the desired skin surface; typically the entire body. Preferably the dispensing means is a sprinkling canister, a spray bottle, or a pre-formed wipe which comprises a flexible dispensing means.

Alternatively, the user may deposit the composition herein onto a wipe comprising a flexible dispensing means of his or her own choosing. To do this, the user chooses a flexible dispensing means such as a washcloth or puff; transfers the composition from a bottle or other suitable container over the chosen flexible dispensing means, and applies the composition to the desired area of the body. The user may also use his/her hand to apply the compositions. The user may use as much or as little of the composition as he/she desires, depending upon their intended use and degree of odor control necessary.

The following non-limiting examples illustrate useful perfume compositions and odor absorbing composition formulations along with methods of use of the present invention. Perfume compositions A–G are all useful for formulating as encapsulated perfume. Perfume compositions E–G may also, optionally, be used as free perfume.

| Ingredients | Wt. % | Ingredients | Wt. % |
| --- | --- | --- | --- |
| PERFUME COMPOSITION A | | PERFUME COMPOSITION B | |
| Ambrox dl 10% in DPG | 1.5 | Benzyl acetate | 2.4 |
| Benzyl acetate | 1.9 | Cinnamic alcohol | 0.1 |
| Benzyl salicylate | 3.1 | cis 3 Hexenyl acetate | 0.3 |
| beta gamma Hexenol | 0.4 | cis Jasmone | 0.4 |
| cis 3 Hexenyl acetate | 0.5 | Citronellol | 4.1 |
| cis-3-Hexenyl salicylate | 2.5 | Citronellyl acetate | 1.3 |
| Citronellal nitrile | 1.5 | Dimethyl octanol | 1.6 |
| Citronellol | 9.2 | Ethyl linalool | 7.3 |
| Cyclal C | 0.9 | Flor acetate | 4.9 |
| Cyclo galbanate | 0.5 | Frutene | 3.3 |
| Dihydro myrcenol | 0.9 | Geraniol | 4.9 |
| Ebanol | 0.1 | Helional | 4.1 |
| Eucalyptol | 0.6 | Hexyl cinnamic aldehyde | 16.0 |
| Eugenol | 0.5 | Hydroxycitronellal | 1.6 |
| Flor acetate | 8.3 | Ionone gamima methyl | 5.7 |
| Frutene | 4.0 | iso E Super | 4.1 |
| Geranyl nitrile | 0.3 | Lyral | 3.3 |
| Hexyl cinnamic aldehyde | 10.5 | Methyl dihydro jasmonate | 16.2 |
| Hydroxycitronellal | 2.3 | Methyl phenyl carbinyl acetate | 0.3 |
| iso Bornyl acetate | 0.2 | P.T.Bucinal | 8.9 |
| iso Cyclo geraniol | 0.6 | Phenyl ethyl alcohol | 4.9 |
| Linalool | 1.9 | Phenyl hexanol | 0.8 |
| Linalyl acetate | 4.2 | Terpineol | 3.3 |
| Methyl cedrylone | 0.2 | Undecylenic aldehyde | 0.2 |
| Methyl dihydro jasmonate | 0.9 | | |
| Methyl iso butenyl tetrahydro pyran | 0.3 | | |
| Methyl phenyl carbinyl acetate | 0.9 | | |
| Orange terpenes | 17.6 | | |
| P.T.Bucinal | 17.8 | | |
| Phenyl ethyl alcohol | 4.6 | | |
| Prenyl acetate | 1.2 | | |
| PERFUME COMPOSITION C | | PERFUME COMPOSITION D | |
| 4-tertiary Butyl cyclohexyl acetate | 10.0 | 4-tertiary Butyl cyclohexyl acetate | 12.3 |
| Bacdanol | 0.5 | Ambrox DL 10% in DPG | |
| Cetalox | 0.1 | Anisic aldehyde | 4.5 |
| Citral | 1.0 | Bacdanol | 0.6 |

-continued

| Ingredients | Wt. % | Ingredients | Wt. % |
|---|---|---|---|
| CitronelloL | 5.0 | cis Jasmone | 0.1 |
| Damascenone | 0.3 | Citronellol | 6.2 |
| Dihydro myrcenol | 1.0 | Ethyl cinnamate | 1.3 |
| Dimethyl benzyl carbinyl acetate | 1.5 | Ethyl vanillin | 1.7 |
| Ethyl vanillin | 0.5 | Eugenol | 0.4 |
| Geraniol | 2.0 | Geraniol | 12.3 |
| Geranyl nitrile | 0.5 | Geranyl acetate | 1.2 |
| Heliotropin | 5.1 | Heliotropin | 12.3 |
| Hexyl cinnamic aldehyde | 15.4 | Hexyl cinnamic aldehyde | 12.3 |
| Ionone gamma methyl | 3.2 | Ionone methyl | 3.5 |
| iso E Super | 3.5 | iso Bornyl acetate | 1.7 |
| Linalyl acetate | 8.1 | iso Eugenol | 0.3 |
| Methyl anthranilate | 1.5 | Lauric aldehyde | 1.2 |
| Methyl dihydro jasmonate | 20.0 | Menthyl acetate | 0.7 |
| Methyl iso butenyl tetrahydro pyran | 0.1 | Methyl anthranilate | 1.5 |
| Orange terpenes | 10.0 | Methyl cinnamate | 1.2 |
| para Methoxy acetophenone | 0.4 | Methyl phenyl carbinyl acetate | 2.7 |
| Vanillin | 10.3 | Phenyl ethyl alcohol | 12.3 |
| | | Undecalactone | 0.6 |
| | | Undecylenic aldehyde | 0.6 |
| | | Vanillin | 6.9 |
| PERFUME COMPOSITION E | | PERFUME COMPOSITION F | |
| Citronellol | 10 | Benzyl salicylate | 20 |
| Benzyl salicylate | 15 | Benzyl acetate | 15 |
| Benzyl acetate | 10 | Benzophenone | 5 |
| Benzophenone | 3 | Phenyl ethyl alcohol | 10 |
| Cedrol | 2 | Linalool | 15 |
| Dihydromyrcenol | 10 | Methyl dihydro jasmonate | 10 |
| Flor acetate | 5 | Lilial | 15 |
| Phenyl ethyl alcohol | 15 | Phenyl ethyl acetate | 5 |
| Linalyl acetate | 4 | | |
| Linalool | 6 | | |
| Methyl dihydro jasmonate | 3 | | |
| Lilial | 10 | | |
| Phenyl ethyl acetate | 2 | | |
| alpha-Terpineol | 5 | | |
| PERFUME COMPOSITION G | | | |
| Citronellol | 5 | | |
| Benzyl salicylate | 5 | | |
| Benzyl acetate | 5 | | |
| Dihydromyrcenol | 5 | | |
| Flor acetate | 5 | | |
| Phenyl ethyl alcohol | 20 | | |
| Linalyl acetate | 5 | | |
| Linalool | 5 | | |
| Methyl dihydro jasmonate | 5 | | |
| Lilial | 20 | | |
| Phenyl ethyl acetate | 1 | | |
| Vanillin | 6 | | |
| alpha-Terpineol | 8 | | |
| Anisic aldehyde | 2 | | |
| Cymal | 3 | | |

| Ingredient | % W/W | Ingredient | % W/W |
|---|---|---|---|
| EXAMPLE I | | EXAMPLE II | |
| Corn Starch (Topical Starch) | 60.80 | Corn Starch (Topical Starch) | 50.00 |
| Silica (Microspheres) | 2.00 | Talc | 10.00 |
| Fumed Silica | 2.00 | Silica (Microspheres) | 3.00 |
| Zinc Phenolsulfonate | 3.00 | Fumed Silica | 1.00 |
| Triclosan | .20 | Zinc Phenolsulfonate | 3.00 |
| Cyclodextrin | 3.00 | Triclosan | 0.30 |
| Aloe Vera, Freeze/Spray Dried | 1.00 | Cyclodextrin | 13.00 |
| Nylon-12 | 5.00 | Aloe Vera, Freeze/Spray Dried | 0.50 |
| Zinc Stearate | 7.00 | Nylon-12 | 5.00 |
| Tocopheryl Acetate Microcapsules | 2.00 | Zinc Stearate | 3.00 |
| Dimethicone | 10.00 | Tocopheryl Acetate Microcapsules | 2.00 |
| Encapsulated Perfume* | 4.00 | Mineral Oil | 2.00 |
| | | Dimethicone | 5.00 |
| | | Free Perfume** | 0.20 |
| | | Encapsulated Perfume* | 2.00 |

-continued

| Ingredient | % W/W | Ingredient | % W/W |
|---|---|---|---|
| EXAMPLE I | | EXAMPLE II | |
| Example I may also comprise a colorant. | | Example II may also comprise a zeolite. | |
| EXAMPLE III | | EXAMPLE IV | |
| Rice Starch | 51.00 | Aluminum Starch Octenyl Succinate (Dry Flo ® Pure) | 30.20 |
| Mica | 2.00 | Silica (Ellipsoids) | 4.00 |
| Silica (Ellipsoids) | 2.00 | Zinc Phenolsulfonate | 7.00 |
| Fumed Silica | 1.00 | Triclosan | 0.60 |
| Triclosan | 0.50 | Cyclodextrin | 10.00 |
| Aluminum Chlorohydrate | 5.00 | Aloe Vera Gel/Oil | 1.00 |
| Cyclodextrin | 6.00 | Zeolite | 10.00 |
| Aloe Vera, Freeze/Spray Dried | 1.00 | Talc | 13.60 |
| Polyethylene Powder | 5.00 | Polyethylene Powder | 7.00 |
| Zinc Stearate | 5.00 | Zinc Stearate | 5.00 |
| Tocopheryl Acetate Oil (Vit. E. Acetate) | 3.00 | Mineral Oil | 5.00 |
| Dimethicone | 10.00 | Dimethicone | 6.00 |
| Nylon N-12 | 5.00 | Free Perfume** | 0.60 |
| Free perfume** | 0.50 | | |
| Encapsulated Perfume* | 3.00 | | |
| Example III may also comprise a zeolite. | | | |
| EXAMPLE V | | EXAMPLE VI | |
| Tapioca Starch | 46.50 | Corn Starch (Topical Starch) | 29.00 |
| Talc | 4.90 | Oat Flour/Colloidal Oatmeal | 16.35 |
| Silica (Microspheres) | 2.50 | Silica (Microspheres) | 2.50 |
| Fumed Silica | 2.00 | Silica (Ellipsoids) | 1.50 |
| Zinc Oxide | 4.00 | Kaolin | 8.00 |
| Triclosan | 1.00 | Zinc Oxide | 2.00 |
| Cyclodextrin | 4.00 | Triclosan | 0.40 |
| Aloe Vera Gel/Oil | 2.00 | Cyclodextrin | 5.00 |
| Nylon-12 | 10.00 | Aloe Vera Gel/Oil | 2.00 |
| Zinc Stearate | 6.00 | Nylon-12 | 4.00 |
| Isopropyl Myristate | 4.00 | Polyethylene Powder | 4.00 |
| Dimethicone | 5.00 | Zinc Stearate | 10.00 |
| Free Perfume** | 0.10 | Tocopheryl Acetate Microcapsules | 5.00 |
| Encapsulated Perfume* | 8.00 | Dimethicone | 10.00 |
| | | Free Perfume** | 0.25 |
| EXAMPLE VI | | | |
| Corn Starch (Topical Starch) | 49.00 | | |
| Kaolin | 14.50 | | |
| Silica (Microspheres) | 2.50 | | |
| Silica (Ellipsoids) | 1.50 | | |
| Fumed Silica | 0.50 | | |
| Zinc Phenolsulfonate | 2.00 | | |
| Triclosan | 0.20 | | |
| Cyclodextrin | 8.00 | | |
| Aloe Vera Gel/Oil | 3.00 | | |
| Nylon-12 | 2.00 | | |
| Polyethylene Powder | 5.00 | | |
| Tocopheryl Acetate Microcapsules | 3.00 | | |
| Isopropyl Myristate | 2.00 | | |
| Dimethicone | 5.00 | | |
| Free perfume** | 0.80 | | |
| Encapsulated Perfume* | 1.00 | | |

*The encapsulated perfume in Examples I–VII may comprise any of the above Perfume Compositions of Examples A–G.
**The free perfume in Examples I–VII may comprise any of the above Perfume Compositions of Examples E–G.

Prepare the above Examples by the following steps: create a first mixture by mixing cyclodextrin, dry ingredients, and a powder carrier in a commercially available mixer such as a vee-blender, double cone blender, or ribbon blender until the mixture is uniform; reduce the particle size of the mixture using a grinding/pulverizing technique such as hammer milling, impact milling, ball milling, or fluid energy milling; and create a second mixture by adding any liquid phase emollients, moisturizers, and/or skin protectants to the mixture, preferably using spray atomization while mixing for a more even dispersion. The second mixture can then undergo a second pulverizing/grinding step, and if desired, an air classifying operation. Where the above Examples include free perfume compositions, creating the second mixture may include the addition of the perfume compositions into the liquid phase. Where the above Examples include encapsulated perfume, the encapsulated perfume may be added with the dry ingredients when creating the first mixture; or, preferably, may be added in a final step of creating a third mixture by adding the encapsulated perfume to the second mixture with mixing.

Preparation for Application to Skin: The compositions of the present invention, such as those formed from the examples may be loaded onto a wipe or deposited into a spray device or canister. The compositions may be applied directly onto the skin or onto a flexible dispensing means of the user's choosing for convenient application to the skin. To prepare wipes, coat, sprinkle, or spray the composition onto a dry flexible dispensing means until desired coating or thickness of composition on the flexible dispensing means is achieved. To prepare spray, deposit the composition into the selected spray package. Close the package for storage until consumer use. To prepare a pressurized aerosol spray, transfer the composition into a suitable container. Pressurize and seal the container after injection of propellant materials.

Example VIII A woman with stress urinary incontinence finds that the wetness associated with this condition causes vaginal odor which she wants to remove from the skin and control. After urinating, the woman wipes her external vagina and pelvic region with a wipe containing the composition in Example I. This woman notices less vaginal odor after using the wipe.

Example IX A large-breasted woman finds that when she exercises, she tends to experience sweating and skin chafing under the breasts. Before and after exercising, she applies the composition from Example IV via a manual spray bottle. She sprays the perfumed composition under her breasts and notices less body odor and feels more comfortable after using the powder spray.

Example X A man has severe allergies to cosmetic deodorants, antiperspirants, and heavy colognes and avoids using such products. This results in uncontrolled and embarrassing body odor. His doctor suggests applying the mild, lightly perfumed odor absorbing composition of Example VI after showering. The man applies the composition to his entire body via a spray each morning after showering, and suffers no allergic reaction. The man feels comfortable without the embarrassment of lingering, uncontrollable body odor. The man keeps a pouch of wipes which also contain the composition of Example VI, for convenient and discreet reapplication as needed.

What is claimed is:

1. A method of reducing body odor comprising the application onto occluded skin of an odor absorbing composition comprising:
   a. from about 0.1% to about 25%, by weight of the composition, of uncomplexed cyclodextrin;
   b. a perfume composition selected from the group consisting of from about 0.05% to about 15%, by weight of the composition, of an encapsulated perfume, from about 0.01% to about 5%, by weight of the composition, of free perfume; and mixtures thereof; and
   c. a powder carrier;
   wherein the encapsulated perfume comprises one or more volatile perfume ingredients each having a boiling point of less than about 260° C., ingredients having significant low detection threshold values, and mixtures thereof.

2. The method of claim 1 wherein the cyclodextrin is selected from the group consisting of beta-cyclodextrin, derivatives of beta-cyclodextrin, alpha-cyclodextrin, derivatives of alpha-cyclodextrin, gamma-cyclodextrin, derivatives of gamma-cyclodextrin, and mixtures thereof.

3. The method according to claim 1 wherein particle sizes are from about 1 micron to about 100 microns.

4. The method according to claim 1 wherein particle sizes are from about 1 micron to about 20 microns.

5. The method according to claim 1 wherein particle sizes of the cyclodextrin are from about 1 micron to about 5 microns.

6. The method of claim 1 further comprising adjunct odor controlling agents selected from the group consisting of zeolites, activated charcoal, sodium bicarbonate, antimicrobial agents, and antiperspirants.

7. The method of claim 1 further comprising skin aids selected from the group consisting of skin protectants, emollients, and moisturizers.

8. The method of claim 1 further comprising slip compounds.

9. The method of claim 1 wherein the composition is delivered using a flexible dispensing means.

10. The method of claim 1 wherein the composition is delivered as a powder by a manually activated spray dispenser.

11. A method of reducing vaginal odor comprising the application to a pelvic region, an external vagina, and/or a panty-area, of a composition comprising:
   a. from about 0.1% to about 25%, by weight of the composition, of uncomplexed cyclodextrin;
   b. a perfume composition selected from the group consisting of from about 0.1% to about 10%, by weight of the composition, of an encapsulated perfume, from about 0.01% to about 5%, by weight of the composition, of free perfume; and mixtures thereof, and
   c. a powder carrier;
   and wherein the encapsulated perfume comprises one or more volatile perfume ingredients each having a boiling point of less than about 260° C., ingredients having significant low detection threshold values, and mixtures thereof.

12. The method of claim 11 wherein the cyclodextrin is selected from the group consisting of beta-cyclodextrin, derivatives of beta-cyclodextrin, alpha-cyclodextrin, derivatives of alpha-cyclodextrin, gamma-cyclodextrin, derivatives of gamma-cyclodextrin, and mixtures thereof.

13. The method according to claim 11 wherein particle sizes are from about 1 micron to about 100 microns.

14. The method according to claim 11 wherein particle sizes of the cyclodextrin are from about 1 micron to about 5 microns.

15. The method of claim 11 further comprising adjunct odor controlling agents selected from the group consisting of zeolites, activated charcoal, sodium bicarbonate, antimicrobial agents, and antiperspirants.

16. The method of claim 11 further comprising skin aids selected from the group consisting of skin protectants, emollients, and moisturizers.

17. The method of claim 11 further comprising slip compounds.

18. The method of claim 11 wherein the composition is delivered using a flexible dispensing means.

19. The method of claim 11 wherein the composition is delivered as a powder by a manually activated spray dispenser.

20. A method of reducing body odor comprising the application onto occluded skin of an odor absorbing composition comprising:

a. from about 0.1% to about 25%, by weight of the composition, of beta-cyclodextrin;

b. a perfume composition selected from the group consisting of from about 0.05% to about 15%, by weight of the composition, of an encapsulated perfume, from about 0.01% to about 5%, by weight of the composition, of free perfume; and mixtures thereof; and c. a powder carrier;

wherein the encapsulated perfume comprises one or more volatile perfume ingredients each having a boiling point of less than about 260° C., ingredients having significant low detection threshold values, and mixtures thereof, and wherein the composition is delivered as a powder by a manually activated spray dispenser.

* * * * *